US006673814B2

(12) United States Patent
Joshi et al.

(10) Patent No.: US 6,673,814 B2
(45) **Date of Patent: *Jan. 6, 2004**

(54) DELIVERY SYSTEMS AND METHODS FOR NOSCAPINE AND NOSCAPINE DERIVATIVES, USEFUL AS ANTICANCER AGENTS

(75) Inventors: Harish C. Joshi, Decatur, GA (US); Keqiang Ye, Lilburn, GA (US); Judith Kapp, Atlanta, GA (US); Jaren Landen, Decatur, GA (US); David Archer, Roswell, GA (US); Cheryl Armstrong, Winnetka, IN (US); Fuqiang Liu, Edison, NJ (US)

(73) Assignee: Emory University, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/056,913

(22) Filed: Jan. 25, 2002

(65) Prior Publication Data

US 2002/0137762 A1 Sep. 26, 2002

Related U.S. Application Data

(63) Continuation-in-part of application No. 09/582,375, filed as application No. PCT/US98/14979 on Jul. 20, 1998, now Pat. No. 6,376,516.

(60) Provisional application No. 60/057,037, filed on Aug. 19, 1997, and provisional application No. 60/264,357, filed on Jan. 26, 2001.

(51) Int. Cl.[7] .......................... A61K 31/445; A61F 2/00

(52) U.S. Cl. ....................... 514/320; 514/319; 424/423; 424/425; 424/450; 424/457; 424/458; 424/459; 424/460; 424/461; 424/462

(58) Field of Search ................................ 514/319, 320; 424/457–462, 450, 425, 423

(56) References Cited

U.S. PATENT DOCUMENTS

| | | | | |
|---|---|---|---|---|
| 3,108,106 A | | 10/1963 | Maillard | 260/285 |
| 4,605,661 A | * | 8/1986 | Hirsch et al. | 514/341 |
| 4,816,462 A | | 3/1989 | Nowicky | 514/279 |
| 4,916,144 A | * | 4/1990 | Strehlke et al. | 514/326 |
| 4,994,281 A | | 2/1991 | Muranishi et al. | 424/497 |
| 5,100,669 A | * | 3/1992 | Hyon et al. | 424/426 |
| 5,213,808 A | * | 5/1993 | Bar-Shalom et al. | 424/473 |
| 6,376,516 B1 | * | 4/2002 | Joshi et al. | 514/320 |

FOREIGN PATENT DOCUMENTS

WO WO 83/00486 2/1986

OTHER PUBLICATIONS

Al–Yuhya et al., "Noscapine", Analytical Profiles of Drug Substances, vol 11 Academic Press, pp. 407–461, 1982.*

Battersby, et al., "Concerning the Biosynthesis of Narcotine", Tetrahedron Lett. 11:669–673, 1965.*

Windholz et al., Editor–in–Chief, The Merk Index, An Encyclopedia of Chemcials, Drugs, and Biologicals, 10th Edition, 1983, pp. 394, 329, 1427–1429.*

Stein, Jay, Editor–in–Chief, Internal Medicine, 4th Edition, Chapters 71–72, pp. 699–715, 1994.*

Al–Yuhya and Hassan, in K.Florey (Ed.), "Noscapine," *Analytical Profiles of Drug Substances*, vol. 11 Academic Press, pp. 407–461 (1982).

Battersby, et al., "Concerning The Biosynthesis of Narcotine," *Tetrahedron Lett.* 11:669–673 (1965).

Empey, D.W., et al., Eur. J. Clin. Pharmacol. 16, 393–397 (1979).

Fleishchhacker, et al., Chem. Monthly 120:765–769 (1989).

Gavrieli, Y. et al., "Identification of Programmed Cell Death in Situ via Specific Labeling of Nuclear DNA Fragmentation," *J. Cell Bio.* 119:493–501 (1992).

Gorczyca, W. et al., "Detection of DNA Strand Breaks in Individual Apoptotic Cells by the in Situ Terminal Deoxynucleotidyl Transferase and Nick Translation Assays," *Cancer Res.* 53:1945–1951 (1993).

Joshi, et al., "y–Tubulin is a centrosomal protein required for cell cycle–dependent microtybule nucleation," Nature, 356:80–83 (1992).

Ke, et al., "Noscapine inhibits tumor growth with little toxicity to normal tissues or inhibition of immune responses," *Cancer Immunol. Immunotherapy*, (2000).

Ke, et al., "Opium alkaloid noscapine is an antitumor agent that arrests metaphase and induces apoptosis in dividing cells," *Proc. Natl. Acad. Sci. USA*, 95:1601–1606 (1998).

Landen, et al., "Noscapine Alters Microtubule Dynamics in Living Cells and Inhibits the Progression of Melanoma," pp. 1–5, figs. 1–4 (unpublished manuscript on file with Emory University School of Medicine, 2001)).

Landen, et al., "The Microtubule Interacting Agent Noscapine for the Treatment of Glioblastoma in Immunodeficient Mice," Cancer Research Abstract Book and on AACR website (2000).

(List continued on next page.)

*Primary Examiner*—Dwayne C. Jones
(74) *Attorney, Agent, or Firm*—Kilpatrick Stockton LLP; Bruce D. Gray

(57) ABSTRACT

The present invention relates to methods useful for the treatment of neoplastic diseases, tumor cells, and the treatment of cancer delivering compounds of the formula

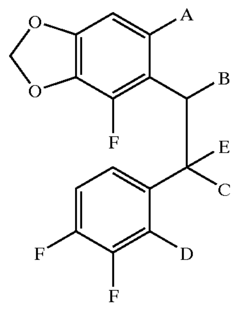

The invention provides various methods of delivering such compounds, combinations of treatments, and altering such compounds to enhance their effectiveness.

21 Claims, No Drawings

OTHER PUBLICATIONS

Landen, et al., Treatment of Murine Melanoma by Noscapine, a Tubulin Interacting Agent, Cancer Research Abstract Book and on AACR website (2001).

Molnar, et al., "In vivro antiproliferative effects of tricyclic psychopharmaceutical agents and synergism with some resistance modifiers," *Anticancer Res.*, 12(1):273–280 (1992).

Moore, M.W., et al., "Introduction of Soluble Protein into the Class I Pathway of Antigen Processing and Presentation," *Cell* 54:777–785 (1988).

Perkin and Robinson, "Synthesis and Resolution of Gnoscopine," *J. Chem. Soc.* [London], 99:775–798 (1911).

Peyrot, V. et al., "Mechanism of Binding of the New Antimitotic Drug MDL 27048 to the Colchicine Site of Tubulin: Equilibrium Studies," *Biochemistry* 31:11125–11132 (1992).

Pinko,C., "Single–chain Recombinant Human Cytomegalovirus Protease," *J. Biol. Chem.*, 270(40):23634–23640 (1995).

Powers, J.C., et al., "Reaction of Porcine Pancreatic Elastase with 7–Substituted 3–Alkoxy–4–chloroisocoumarins: Design of Potent Inhibitors Using the Crystal Structure of the Complex Formed with 4–Chloro–3–ethoxy–7–guanidinoisocoumarin," *Biochemistry* 29:3108–3118 (1990).

Prior, S.; "Borane adducts of narcotine, hydrastine and their reduction products," *Arch. Pharm.* 316(9):737–746 (1983) (chemical Abstracts vol. 99, 176115z (1983).

Sam, J. et al., "Preparation and Properties of Some Relatives of Noscapine," *J. Pharm. Sci.* 57:–1755–1759 (1968).

Shono, T. et al., "New Electroreductive Synthesis of Phthalide Alkaloids," *Tetrahedron Lett.*, 21:1351–1354 (1980).

Uchegbu, "Science in Pharmacy Parenteral drug delivery," *Pharmaceutical Journal*, 263(7061):355–358 (1999) and www.pharmj.com/Editorial/19990904/education/parenteral2.html.

Uchegbu, et al., "Science in Pharmacy, Parenteral drug delivery: 1," *Pharmaceutical Journal*, 263(7060):309–318 (1999).

Walton, M.I. et al., "Constitutive Expression of Human Bcl–2 Modulates Nitrogen Mustard and Camptothecin Induced Apoptosis," *Cancer. Res.* 53:1853–1861 (1993).

Witt, et al., "Peptide drug modifications to enhance bioavailablity and blood–brain barrier permeability," *Peptides*, 22:2329–2343 (2001).

"Noscapine," Chemcial Abstracts, p. 1063 No. 6638.

"Offering Hope in the Treatment of Brain Cancer," http://www/gliadel.com (Jan. 16, 2002) (16 pages).

"The Brain Infusion Kit and Brain Infusion Kit II," http://www.alzet.com/products/products–sec05.html (Jan. 16, 2002) (2 pages)).

"In Vivo Pharmacology," http://www.alzet.com/products/products–sec03.html (Jan. 16, 2002) (2 pages).

"A General Description," http://www/alzet.com/products/procucts–sec01.html (Jan. 16, 2002) (1 page).

"DUROS®," http://www.durect.com/wt/durect/page–name/duros (Jan. 22, 2002) (2 pages).

"BBBD Therapy," http://www.ohsu.edu/hosp–bbb/bbbd-therapy.html (Jan. 22, 2002) 3 pages).

"The Microtubule Interacting Agent, Noscapine, for the Treatment of Glioblastoma and Melanoma," New Data, Department of Cell Biology, Emory University, Joshi Laboratory (undated).

Perry, Michael, *Chemotherapy Source Book*, (Williams & Wilkins 2d ed., 1997).

Sim, "Medicinal Plant Alkaloids," $2^{nd}$ Ed. Un. Toronto Press, p. 70 (1970).

Uhrin, et al., *Collect. Czech. Chem. Communc.* 54:498 (1989).

* cited by examiner

DELIVERY SYSTEMS AND METHODS FOR NOSCAPINE AND NOSCAPINE DERIVATIVES, USEFUL AS ANTICANCER AGENTS

This application is a continuation in part of U.S. Ser. No. 09/582,375 now U.S. Pat. No. 6,376, 516 entitled "Noscapine and Noscapine Derivatives, Useful as Anti-Cancer Agents" filed Sep. 26, 2000 which is also a 371 of PCT/US98/14979 that has a filing date of Jul. 20, 1998, which claimed benefit of U.S. Provisional Application No. 60/057,037 filed Aug. 19, 1997. This application also claims benefit of U.S. Provisional Application No. 60/264,357 entitled "Noscapine and Noscapine Derivatives, Useful as Anti-Cancer Agents" filed Jan. 26, 2001. The entire contents of each of the above-referenced applications are incorporated herein by reference.

The subject matter of the present invention was supported in part by one or more grants from the United States Government, GM51389 and CA70372.

BACKGROUND OF THE INVENTION

1. Field of the Invention

The present invention relates to delivery systems and methods useful for the treatment of neoplastic diseases, and to combinations of treatments useful for the treatment of neoplastic diseases.

2. Description of Related Art

Two important events in the cell division cycle are the duplication of the chromosomal DNA and the separation of the duplicated chromosomes. These events occur in two discrete phases: the synthetic phase (S-phase) and the mitotic phase (M-phase), which are separated from each other by distinct gaps in time, gap 1 (G1) and gap 2 (G2). The proper coordination of these events is achieved by checkpoint pathways that delay the progression of the cell cycle when proper completion of one phase is disrupted by physical damage or other means. Under normal circumstances, if the extent of damage is irreparable, most cells initiate a sequence of biochemical events leading to programmed cell death or apoptosis. Deregulation in any one or more of these checkpoint mechanisms sometimes leads to genetic instability which is a primary step for a tumor to evolve into invasive malignant state. The chemotherapeutic management of various cancers is achieved by drugs that block either the S-phase, the M-phase, or that block regulatory or metabolic pathways impinging upon the cell cycle machinery.

For example, some drugs affect the functions or structures of DNA or RNA, others interfere with enzymes involved in folate, purine, or pyrimidine metabolism, or the function of mitotic spindles. Anti-mitotic drugs such as vinica akaloids and taxoids can arrest cells in M-phase by interacting with mitotic spindle components, microtubules. Microtubules are one of the major filamentous components of the cytoskeleton, and, together with actin and intermediate filaments, they organize the cellular cytoplasm. In interphase cells, a dynamic radial array of microtubules emanates from the centrosome at the cell center. In this array, the fast growing and fast shrinking plus ends of microtubules project distally from the center.

During mitosis, the duplicated centrosomes nucleate assembly of much more dynamic and more numerous polymers as they move apart to form the opposite poles of the mitotic spindle. The increased dynamics and number of microtubules enhance the chance-encounter of growing microtubules with the primary construction of the duplicated chromatid pairs. Upon attaching to microtubules, chromosomes undergo a series of movements eventually leading to their conversion and final assembly at the mid-plate during metaphase. The onset of the next event in mitosis, the anaphase, is delayed until each of the chromatid pairs is assembled at the metaphase mid-plate and proper tension is generated on the attached sister chromatids.

Dynamic assembly or disassembly of microtubules is required for the morphogenesis of mitotic spindle. Accordingly, small organic molecules that modulate the dynamics of microtubules primarily because some of the microtubule interacting agents are useful for chemotherapeutic management of certain kinds of tumors. There are two classes of these anti-microtubule agents: those that prevent the assembly of tubulin, and those that promote the assembly of tubulin. A prototypic example of a potent assembly inhibitor is colchicine. Others are analogs of colchicine such as podophyllotoxin, MTC [(2-methoxy-5-(2,3,4-trimethoxyphenyl)-2,4,6-cycloheptatrien-1one)], TCB (2,3,4-trimethoxy-4'-carbomethoxy-1, 1'-biphenyl) and TKB (2,3,4-trimethoxy-4'-acetyl-1,1'-biphenyl), and vinica akaloids. Taxol and its analogs represent a class of compounds that promote the assembly of microtubules. It is now clear that although all of these microtubule drugs prevent cell division, only a select few have been useful clinically. In addition, there are differences regarding the toxicity and the efficacy of these drugs for distinct classes of tumors.

SUMMARY

Applicants have discovered that the antitussive noscapine and its derivatives are useful in the treatment of neoplastic diseases. Noscapine is used as an antitussive drug and has low toxicity in humans. Noscapine arrests mammalian cells at mitosis, causes apoptosis in cycling cells, and has potent antitumor activity. Noscapine is an alkaloid from opium, and is readily available as a commercial byproduct in the commercial production of prescription opiates. Applicants have unexpectedly discovered that noscapine promotes assembly of tubulin subunits.

Applicants have synthesized derivatives of noscapine, a known antitussive having low toxicity in humans, and have shown they promote assembly of tubulin subunits, a characteristic suitable for the treatment of tumors and various neoplastic diseases.

In one embodiment of the invention, Applicants provide delivery systems and methods for the treatment of neoplastic diseases. For example, one delivery system according to an embodiment of this invention comprises a composition comprising noscapine or a noscapine derivative and a controlled-release mechanism to enhance delivery of the composition. In a further embodiment, Applicants provide a method for the treatment of neoplastic diseases wherein noscapine and its derivatives can be delivered in combination with another tumor therapy for the treatment or prevention of tumors.

DETAILED DESCRIPTION OF SPECIFIC EMBODIMENTS OF INVENTION

One embodiment of the present invention relates to systems and methods for the treatment of neoplastic diseases, comprising a composition comprising a compound of the formula

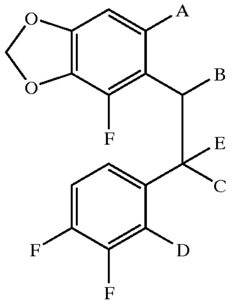

wherein:

1. A is (i) 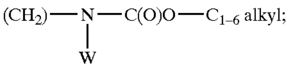

and W is $C_{1-6}$ alkyl;

(ii) 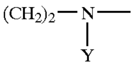

and forms a six membered ring with B, said ring containing one nitrogen;

Y is (a) $C_{1-6}$ alkyl, or H;

(b) C(O)—$C_{1-6}$ alkyl;

(c) 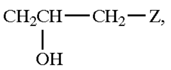

wherein Z is $C_{1-6}$ alkyl or O-$C_{1-6}$ alkyl or O-$C_{1-6}$ alkyl;

(d) aryl; or (e) heterocycle;

B is a single bond, OH or halo;

C is —OH, —$CH_2$—, —O—, or forms a 5-membered lactone or lactam ring with D; and D is:

(i) —OH, —$CH_2$-halo, —CH(O)—, —COOH, —C(O)—O—$C_{1-6}$ alkyl, —$(CH_2)_n$—,—CHOH—, wherein n is an integer and is 1,2, or 3; or (ii) forms a 5-membered lactone or lactam ring with C;

E is —H or —$CH_3$; and

F is —OH or —$OCH_3$, or pharmaceutically acceptable salts thereof, and a controlled-release mechanism, whereby the delivery system enhances the delivery of the composition to a patient in need thereof.

Examples of controlled-release mechanisms suitable for use in the delivery system of the invention include, but are not limited to implantable devices, delivery pumps, wafers, gels, lotions, topical applications, and combinations thereof. Other examples of controlled-release mechanisms include but are not limited to controlled-release formulations comprising a modified compound. For the purposes of this document, "modified" means chemically changed, associated with, combined with, mixed with, delivered with, encapsulated by, caged, protected, lipidized, structurally modified to enhance stability, glycosylized, combined with nutrient transporters, used as a prodrug, incorporated with vector-based strategies, cationization, polymer conjugation, or combinations thereof, such that the compounds is at least partially altered from the above structure.

For example, controlled-release mechanisms may include but are not limited to the compound being caged, protected, or otherwise modified forms of the compound, such as modification to enhance its permeability through a patient's blood-brain barrier, modifications to the compound for tumor targeting purposes, and combinations thereof.

An example of a preferred compound that may be used in the delivery systems or methods of this invention is:

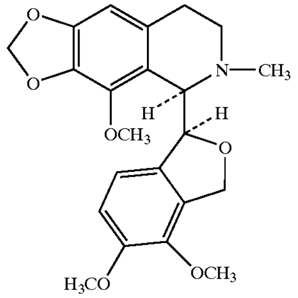

or pharmaceutically acceptable salt thereof.

Another embodiment of the present invention also relates to a method for the treatment of neoplastic diseases, comprising administering to a mammal in need of such treatment an effective amount of a composition comprising a compound of the formula

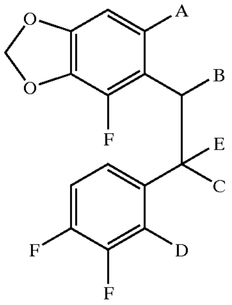

wherein:

A is (i) 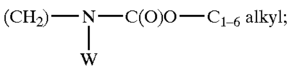

and W is $C_{1-6}$ alkyl;

(ii) 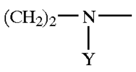

and forms a six membered ring with B, said ring containing one nitrogen;

Y is (a) $C_{1-6}$ alkyl, or H;

(b) C(O)—$C_{1-6}$ alkyl;

(c) 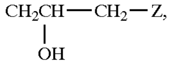

wherein Z is $C_{1-6}$ alkyl or O—$C_{1-6}$ alkyl;

(d) aryl; or (c) heterocycle;

B is a single bond, OH or halo;

C is —OH, —$CH_2$—, —O—, or forms a 5-membered lactone or lactam ring with D; and D is:

(i) —OH, —$CH_2$-halo, —CH(0)—, —COOH, —C(O)—O—$C_{1-6}$ alkyl, —$(CH_2)_n$—, —CHOH—, wherein n is an integer and is 1,2, or 3; or (ii) forms a 5-membered lactone or lactam ring with C;

E is —H or —$CH_3$; and

F is —OH or —$OCH_3$, or pharmaceutically acceptable salts thereof, in combination with a tumor therapy.

Exemplary tumor therapies include but are not limited to radiation therapy, phototherapy, surgical resection, immunotherapy, vaccination, interferon treatment, chemotherapy, stereotactic surgery, such as Gamma Knife® surgery, and combinations thereof.

An example of a preferred compound that may be used in the delivery systems or methods of this invention is:

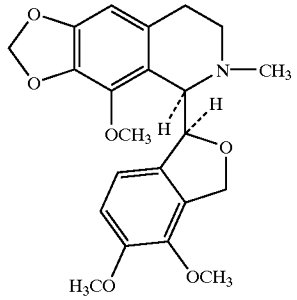

or pharmaceutically acceptable salts thereof.

Other embodiments of the present invention relate to a method for the treatment of neoplastic diseases, comprising administering the compositions described above via oral delivery, rectal delivery, nasal delivery, parenteral delivery, subcutaneous delivery, intravenous delivery, intramuscular delivery, intraperitoneal delivery, infrasternal injection, infusion, direct tissue injection, topical delivery, intracranial delivery and combinations thereof.

The compounds of the present invention, may have asymmetric centers and occur as racemates, racemic mixtures and as individual diastereomers or enantiomers, with all isomeric forms being included in the present invention.

When any variable (e.g., W, Y, A, B, C, etc.) occurs more than one time in any constituent or in formula I, its definition on each occurrence is independent of its definition at every other occurrence. Also, combinations of substituents and/or variables are permissible only if such combinations result in stable compounds. As used herein except where noted, “alkyl” is intended to include both branched-and straight-chain saturated aliphatic hydrocarbon groups having the specified number of carbon atoms (Me is methyl, Et is ethyl, Pr is propyl, Bu is butyl); “Halo” as used herein means fluoro, chloro, bromo and iodo. As used herein, with exceptions as noted, “aryl” is intended to mean phenyl (Ph) or naphthyl.

The term heterocycle or heterocyclic, as used herein except where noted, represents a stable 5-to 7-membered mono-or bicyclic or stable 7-to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include but are not limited to piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl.

The pharmaceutically-acceptable salts of the compounds of the present invention (in the form of water-or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methansulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Synthesis of Noscapine

Noscapine is an alkaloid occurring in abundance in the opium plant, Papaver somniferum L. papaveraceae. It can be extracted from the water-insoluble residue remaining from the processing of opium in the commercial synthesis of morphine. It is readily available commercially in large quantities at low cost, from e.g., Aldrich Chemical Co., or Sigma Chemical Co. Noscapine can be separated from other opium alkaloids by the procedure according to Al-Yuhya, M. A. et al., in K. Florey (Ed.) Analytical Profiles of Drug Substances, Vol. 11 Academic Press 1982, pp. 407-461, or Sim, S. K. "Medicinal Plant Alkaloids," 2nd Ed. Un. Toronto Press 1970, p. 70.

Chemical synthesis of noscapine 1 is less desirable, although feasible. See, for example, Fleischhacker, W. et al. Chem. Monthly 120, 765 (1989); Shono, T. et al. Tetrahedron Lett. 21, 1351 (1980).

There are a variety of methods to synthesize noscapine. A one step synthetic reaction was published by W. H. Perkin and R. Robinson, *J. Chem. Soc.* [London], 99, 775 (1911). However, this method gave low yield and racemic mixtures. The reaction is shown as follows:

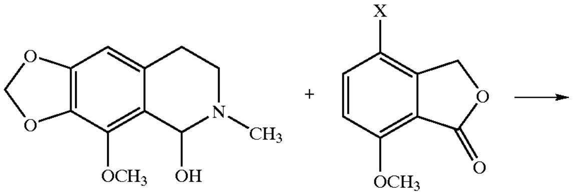

10

(X = H, Cl, Br, $NO_2$)

11

-continued

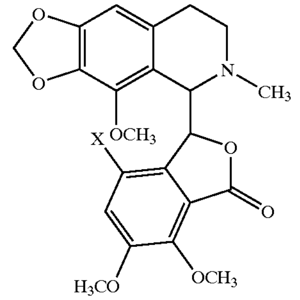

(X = H, Cl, Br, $NO_2$)

12

A second method was published by Von P. Kereks and R. Bognar. *J. Prakt. Chem.* 313, 923–928 (1971). In this method, 2-(3'-methoxy-4',5'-methylenedioxy-phenyl) ethylamine 13 reacts with meconine-3-carbonyl chloride 14 in benzene to gove N-(β-3-methoxy-4,5-methylenedioxyphenylethyl)-mekonine-3-carbonylamide 15 with a yield of 86.6%. Compound 15 was cyclized by boiling with $POCl_3$ for 5 hr to produce compounds 16 and 17 with a yield of 46.7%. Compounds 16 and 17 are two isomers from cyclization of compound 15. These two isomers are reduced by either $H_2/PtO_2$ in acetic acid, or $NaBH_4$ in methanol. The reduced compound 18 was methylated by boiling with the mixture of HCHO and HCOOH, to produce noscapine 1 with a yield of 20.3%.

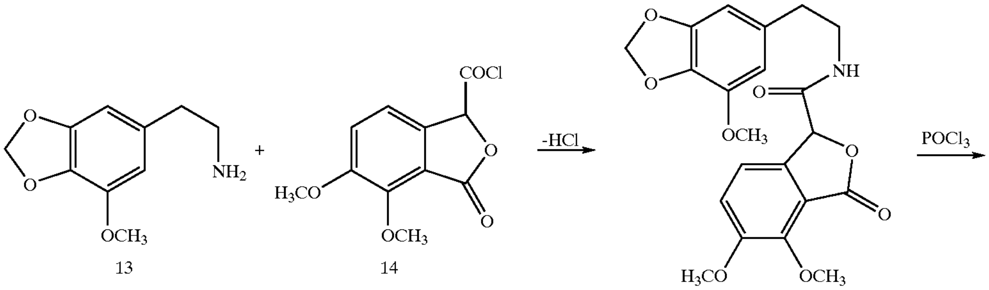

13 14 15

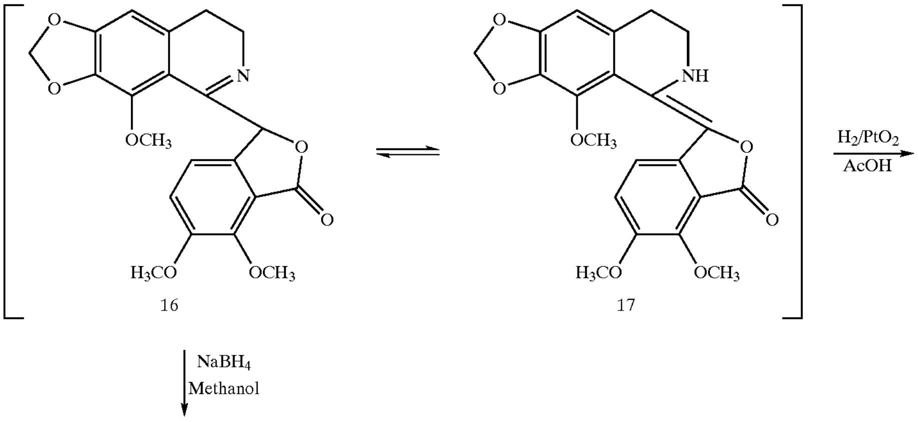

16 17

-continued

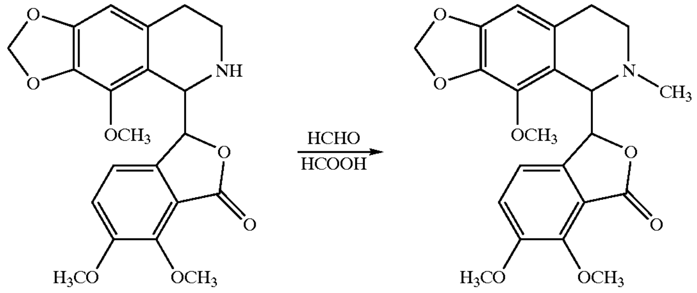

18

(X = H, Cl, Br, $NO_2$)

1

The compounds of the present invention are generally useful in the treatment of tumor cells and a variety of cancers, including but not limited to cancer of the colon, non-small cell lung cancer, cancer of the brain, ovarian cancer, cancer of the kidney, cancer of the prostate, leukemia, breast cancer, skin cancer, melanoma, and cancer of the bladder. For most of these kinds of neoplastic diseases, applicants have tested a variety of cell lines with noscapine, or derivatives thereof. The compounds of the present invention are generally delivered in dosage unit formulations containing conventional non-toxic pharmaceutically-acceptable carriers, adjuvants and vehicles.

One embodiment of the invention relates to the discovery that noscapine has been found to inhibit the progression of melanoma. Specifically, the present inventors have determined that noscapine is effective against tumors derived from malignant melanoma cells, a tumor considered to be refractory to chemotherapy. Noscapine suppresses microtubule dynamics in cells. It increases the pause duration by from about 54% to about 244% and decreases the rate of microtubule shortening by about 20% to about 90%. This treatment procedure led to about an 83% reduction of tumor volume compared to untreated animals. In other words, the present inventors have determined that noscapine, and most likely noscapine derivatives, prevents a number of dynamic events in the life history of a microtubule, without affecting its long term existence, and that noscapine and its derivatives is effective in selectively inhibiting tumor growth.

Without wishing to be bound to any theory, it appears that minor pertubations in microtubule dynamics can engage a mitotic checkpoint, arresting cells in mitosis. The loss of mitotic checkpoints in tumor cells might, in fact, be a very common occurrence associated with cancer. Cells that lack mitotic checkpoints are highly sensitive to mitotic stress caused by microtubule targeting agents, leading to the appreciation that checkpoint loss might contribute positively toward chemotherapeutic outcome for some cancers. See Landen, J. W., et al., Noscapine Alters Microtubule Dynamics in Living Cells and Inhibits the Progression of Melanoma (2001) (unpublished manuscript, on file with Emory University School of Medicine), incorporated herein in its entirety by this reference.

Another embodiment of the invention relates to delivery systems and methods for delivering the compounds of the present invention via a controlled-release mechanism. For example, if the compounds of this invention can be administered via a time-release mechanism or can be altered or modified such that the compound itself is adapted for controlled-release, its activity and therapeutic effect may be prolonged.

In one embodiment, the compounds are delivered via controlled-release mechanisms such as time-release devices. Such controlled-release mechanisms may include, but are not limited to, implantable devices, delivery pumps, wafers, biodegradable polymers, gels, lotions, topical applications, and combinations thereof. For example, implantable devices such as osmotic pumps may be implanted to continuously deliver drugs at controlled rates. Such pumps can be implanted subcutaneously or intraperitoneally, and can be designed for targeted delivery, i.e., to a particular tissue or organ, or for general delivery.

One example of such a pump is the ALZET® osmotic pump. These pumps are used in the research setting and are implanted into research animals to maintain certain plasma concentrations of a drug at certain levels. Another example of such a pump is the DUROS® pump. This pump operates like a miniature syringe loaded with a drug inside the drug reservoir. Through osmosis, water from the body is slowly drawn through a semipermeable membrane into the pump by salt residing in the engine compartment. This water fills the pump, which slowly and continuously pushes a piston, dispensing the correct amount of drug out the drug reservoir and into the body. Such osmotic engines do not require batteries, switches or other electromechanical parts in order to operate. The amount of drug delivered by the system is regulated by the membrane's control over the amount of water entering the pump and by the concentration of the drug in the drug reservoir.

It is preferable that the controlled-release mechanism be adapted to deliver the composition at the desired dosing rate with a high degree of precision. It is also preferable that the system protect the composition from degradation by enzymes and its passage through the body so that the system is not required to be removed and replaced continuously. In most instances, the controlled-release mechanism is placed just under the skin, for example in the upper arm.

Controlled-release mechanisms may be used that are systemic or adapted for site-specific administration of the composition. For example, to deliver a drug to a specific site, the company manufacturing the DUROS® system is developing miniaturized catheter technology that can be attached to the system to direct the flow of a drug to the target organ, tissue or synthetic medical structure, such as a graft. Site specific delivery enables a therapeutic concentration of a drug to be administered to the desired target without exposing the entire body to a similar dose.

Although specific controlled-release mechanisms have been described, it is understood that any implantable controlled-release mechanisms that can be used to deliver noscapine or its derivatives is considered within the scope of this invention. For example, implantable delivery devices are also currently used in some patients to deliver birth control over an extended period of time. Such implants or similar implantable devices used to deliver noscapine or its derivatives are time-release mechanisms within the scope of this invention.

Another controlled-release mechanism for use with the present invention is a wafer. Wafers can be provided in various sizes and various materials and delivered directly to a surgical cavity. For example, after a tumor has been resected, a wafer may be placed in the resulting cavity. Additionally or alternatively, a wafer may be implanted on or near an area of a tumor. One example of a wafer currently available is the Gliadel® wafer. This wafer contains carmustine, and up to eight wafers are implanted in a cavity when a brain tumor is surgically removed. The wafer delivers chemotherapy directly to the site of a tumor.

According to various embodiment of the present invention, any number of wafers containing noscapine or its derivatives can be implanted in a surgical cavity, on or near a tumor, or any combination thereof, in order to deliver noscapine or its derivatives to a patient in need thereof. For example, after brain surgery, a wafer containing noscapine or its derivatives may be implanted in the surgical cavity. This may be used in conjunction with other controlled-release mechanisms described herein. Alternatively, after a mastectomy, a wafer containing noscapine or its derivatives may be implanted in the surgical cavity. This concept is envisioned for use during any type of tumor resection.

In an alternate embodiment of the invention, the controlled-release mechanism is a biodegradable matrix or polymer. The composition of this invention can be complexed, mixed with, or otherwise associated with a matrix or polymer that can be injected into or just under a patient's skin. As the matrix or polymer slowly degrades over time, more and more of the active composition can be released. Examples of such matrixes or polymers are currently known in the art.

In another embodiment of the invention, noscapine or its derivatives is delivered topically, for example, via a gel, a lotion, or a patch. In some aspects, a gel or lotion may be applied topically, i.e., directly to a patient's skin on or near the site of, for example, a skin tumor. In a preferred embodiment, the gel or lotion has controlled-release beads or capsules contained therein. One skilled in the art would be knowledgeable about how to prepare such compositions. However, even without such beads or capsules, a noscapine or noscapine derivative gel or lotion should be considered a controlled-release mechanism within the scope of this invention: the patient may apply a light layer to the skin or may apply a heavier layer that will take longer to absorb, thus at least partially controlling the release of the composition. Additionally or alternatively, the gel or lotion may be applied orally, rectally, nasally, or combinations thereof.

Another topical application for use with another embodiment of this invention is a noscapine or noscapine derivative patch. The composition may be included in a patch for delivery through the skin. Patches of this type are known in the art any may include additional skin penetrating enhancers.

A further embodiment includes the delivery of noscapine or its derivatives via iontophoresis. Specifically, the number of drugs that may be delivered by the transdermal route is limited by the barrier properties of the skin. Conventional transdermal therapy is traditionally limited to small, potent and lipophilic drugs. Iontophoresis is one strategy that facilitates transdermal drug delivery. Iontophoresis is facilitated movement of ions across a membrane, e.g. the skin in order to deliver a positively charged drug across the skin. In this embodiment, a solution of, for example, a cationic formulation of noscapine or its derivatives may be placed at the positive electrode where it is repelled and then attracted towards a negative electrode place elsewhere on the body.

Additional or alternative controlled-release mechanisms for use with this invention comprise a controlled-release formula of the compound. In other words, the controlled-release mechanism may comprise a modification or alteration of the compound itself. For example, the controlled-release mechanism may comprise caged, protected, or modified forms of noscapine or its derivatives for efficient or enhanced delivery and/or later activation purposes. This embodiment relates to the use of prodrugs in cancer chemotherapy to target relatively toxic compounds to specific areas of pathology. This controlled-release mechanism allows more efficient release of the compound into the specific area of pathology sought to be treated. Two technologies that are particularly relevant to this invention are antibody directed enzyme prodrug therapy (ADEPT) and the use of polymeric prodrugs (commonly known as polymer drug conjugates).

As described by Ijeoma F. Uchegbu, *Parenteral drug delivery*: 2, PHARMACEUTICAL JOURNAL, Sep. 4, 1999, at 355, incorporated herein by this reference, (also at www.pharmj.com/Editorial/19990904/education/parenteral2.html), the principle behind the ADEPT approach is that an antibody-enzyme conjugate is administered intravenously, localizes in tumor tissue, and subsequently activates an administered prodrug predominantly within such tumors. Prodrug activation occurs on the cell surface or in the extracellular fluid, which is in different from the polymeric prodrug approach, where prodrug activation occurs intracellularly. The appearance of the active drug after prior administration of the antibody-enzyme conjugate to patients confirms the feasibility of the ADEPT approach. In some instances, to promote specificity, a non-human, e.g., bacterial, enzyme such as carboxypeptidase G2 is used to activate the prodrug. Because such enzymes may also elicit an immune response, it may also be necessary to administer an immunosuppressant. Preferably, the prodrug should be nontoxic and the enzyme should locate only at tumor sites. The use of noscapine or its derivatives in conjunction with research in this area to treat neoplastic diseases is considered within the scope of this invention.

This article also describes the use of polymeric prodrugs, which involves the use of an active substance and possibly a targeting moiety, both linked via spacers to a water-soluble polymeric backbone. From this basic configuration, a number of polymer drug conjugates for cancer chemotherapy have been synthesized with cleavable drug polymer linkers.

Polymer drug conjugates accumulate selectively within tumor tissue and leak through the disorganized vasculature. Clearance from tumor tissue is delayed due to the poor lymphatic drainage, thus tumor accumulation of polymer drug conjugates has been called the enhanced permeation and retention effect. On IV administration the conjugate is taken up by tumor cells and the active drug released intracellularly.

Most of the polymeric backbones that have been studied are prepared from non-biodegradable materials. Although in some instances, biodegradable polymers may be more acceptable, care must be taken to ensure that biodegradation does not hamper the accumulation of conjugates in tumor tissue.

The use of polymer drug conjugates is believed to improve the activity of anticancer agents. Polymer drug conjugates also decrease distribution to potential sites of toxicity. By targeting certain compounds away from sites of potential toxicity, polymer conjugates can significantly increase the maximum tolerated dose of a compound in patients. The use of noscapine or its derivatives in conjunction with research in this area to treat neoplastic diseases is considered within the scope of this invention.

In an even further embodiment of this invention, the controlled-release mechanism for noscapine or its derivatives enhances the permeability of the composition through a patient's blood-brain barrier in order to treat brain tumors. This may be done through any number of methods. Examples include, but are not limited to disruption of the blood brain barrier, receptor-mediated mechanisms, and liposomal encapsulation.

For example, it has been reported that temporarily opening the blood-brain barrier can allow chemotherapeutic agents to pass into the brain and reach the tumor. See, e.g., www.ohsu.edu/hosp-bbb/bbbdtherapy.html. Specifically, the brain's protective barrier is composed of tightly knit endothelial cells, which line the walls of the blood vessels in the brain. These tightly knit cells create a barrier that blocks the entry of various substances, including many therapeutic agents. By temporarily shrinking these cells with a concentrated sugar solution, the barrier can be opened, allowing chemotherapy drugs, such as noscapine or its derivatives, to pass into the brain and reach the tumor. It has been found that compared with standard chemotherapy, blood-brain barrier disruption therapy increases the delivery of the chemotherapy drugs to the tumor and its surrounding area around the tumor by tenfold to a hundredfold.

Another embodiment includes using peptide drug transporters linked to, or otherwise associated with, noscapine or its derivatives to enhance access to the brain. It has been found that various peptide drug modifications can enhance bioavailability and blood-brain barrier permeability. See, e.g., Ken A. Witt, et al., *Peptide Drug Modifications to Enhance Bioavailability and Blood-Brain Barrier Permeability*, 22 PEPTIDES 2329 (2001), incorporated herein by reference. This article discusses modifications such as lipidization, structural modification to enhance stability, glycosylation, use of nutrient transporters, prodrugs, vector-based strategies, cationization, and polymer conjugation.

The embodiment related to modifying noscapine or its derivatives by receptor-mediated mechanisms includes altering noscapine or its derivatives or packaging it into an agent that is capable of binding to tumor cell receptors and therefore selectively entering tumor cells. This embodiment would enable researchers to target these agents specifically to tumor cells by drugs with high biological activity and a low incidence of side effects since the drug would only enter cells with appropriate receptors.

The embodiment related to liposomal encapsulation includes noscapine or its derivatives encapsulated liposomally, enabling it to readily permeate lipid rich cell membranes and enhance its delivery to cells. Liposomes are formed by the self-assembly of phospholipid molecules in an aqueous environment. The amphipathic phospholipid molecules form a closed bilayer sphere in an attempt to shield their hydrophilic groups from the aqueous environment, while still maintaining contact with the aqueous phase via the hydrophilic head group. The resulting closed sphere may encapsulate aqueous soluble drugs, such as noscapine or its derivatives, with the bilayer membrane.

Alternatively, lipid soluble drugs may be complexed with cyclodextrines and subsequently encapsulated within the liposome aqueous compartment. Drugs encapsulated within or associated with liposomes in this way alters drug pharamacokinetics and may be useful in various targeted therapies. These concepts may be used in conjunction with noscapine or its derivatives in order to optimize liposomal drug targeting and delivery. For example, the reduced liver and spleen uptake of stealth liposomes (as polyoxyethylene liposomes came to be known) is believed to be due to a reduced coating recognition by the liver and spleen and enjoy long circulation times.

Another embodiment of this invention relates to noscapine or its derivatives modified with tumor specific antibodies, ligands for tumor specific proteins, or as an adduct for the compound or its derivatives for tumor targeting purposes. For example, tumor associated antigens ("TAA") are highly, homogeneously, frequently and selectively expressed on the cell surface in clinical tumor samples and represent potentially excellent targets for tumor immunotherapy. The use of antibodies selective for TAA or other ligands for tumor specific proteins added to noscapine or noscapine derivative structures is believed to enable the precise targeting of those agents to tumor tissue.

In an additional or alternate embodiment, the compounds of the present invention may be delivered in combination with additional, more common, tumor or cancer therapies. For example, noscapine or noscapine derivatives may be used as a preventive measure after surgical excision or in combination with other anti-cancer treatments. For instance, noscapine or its derivatives may be delivered in combination with radiation therapy, phototherapy, surgical resection, immunotherapy, vaccination, interferon treatment, chemotherapy, stereotactic surgery, such as Gamma Knife® surgery, and combinations thereof. Some classes of chemotherapy include but are limited to: covalent DNA binding drugs, anti-metabolites, anti-tumor antibiotics, microtubule-targeting drugs, DNA-based topoisomerase inhibitors (I and II), differentiation agents, hormonal agents, enzymes, and any combination thereof. Further examples and descriptions are provided in MICHAEL C. PERRY, CHEMOTHERAPY SOURCE BOOK (Williams & Wilkins 2d ed. 1997), incorporated herein by reference.

These treatments are merely provided as examples and are not intended to be exhaustive of the possible cancer treatments available not intended to limit the present invention. It is anticipated the cancer researchers will invent and/or discover other therapies that may be used to treat tumors, and noscapine or its derivatives used in combination with such treatments to treat neoplastic diseases is considered within the scope of this invention.

In a further embodiment, the compounds of the present invention may be administered orally, rectally, nasally (for example, by inhalation spray), parenterally (including subcutaneous injections, intravenous, intramuscular, infrasternal injection or infusion techniques), intraperitoneal delivery, direct tissue injection, topical delivery, and combinations thereof.

These pharmaceutical compositions may be in the form of orally-administrable suspensions or tablets; nasal sprays; sterile injectable preparations, for example, as sterile injectable aqueous or oleaginous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono-or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidity and/or dissolve in the rectal cavity to release the drug.

When delivered as a topical formula, the compositions may be prepared with any gel or lotion substrate commonly known in the field of topical drug delivery. Such preparations would be apparent to those of skill in the art.

Thus, in accordance with the present invention there is further provided a method of treating and a pharmaceutical composition for treating tumor cells and related cancers. The treatment involves administering to a patient in need of such treatment a pharmaceutical composition comprising a pharmaceutical carrier and a therapeutically effective amount of a compound of the present invention, or a pharmaceutically acceptable salt thereof.

Doses and dosage levels will vary depending upon the state of the condition treated, the delivery route chosen, and other physical considerations. In one embodiment, dosage may range of the order of 0.02 to 5.0 or 10.0 grams-per-day, which has been found useful in the treatment or prevention of the above-indicated conditions, with oral doses two-to-five times higher. For example, compound 4 is effectively treated by the administration of from 10 to 50 milligrams of the compound per kilogram of body weight from one to three times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLE 1

Synthesis of Noscapine

Noscapine 1 was synthesized by the methods of Shono, T. et al., Tetahedron Lett. 21, 1351 (1980); Fleishchacker, W. et al., Monatshefte fur Chemie 120, 765 (1989); Sam, J. et al., J. Pharm. Sci. .57: 1755 (1968); Al-Yuhya. M. A. et al., in K. Florey (Ed.) Analytical Profiles of Drug Substances, Vol. 11 Academic Press 1982, pp. 407–461; Battersby, A. R. et al., Tetrahedron Lett. 11, 669 (1965). It is readily available in large qantities from a variety of commercial sources, e.g. Aldrich Chemical Co. or Sigma Chemical Co.

NMR data for (S, R)-Noscapine $^1$H NMR ($CDCl_3$, 300 MHz): δ6.95 (d, J=8.1 Hz, 1 H), 6.27 (s, 1 H), 6.07 (d, J=8.4 Hz, 1 H), 5.90 (s, 2 H), 5.55 (d, J=3.9 Hz, 1 H), 4.37 (d, J=4.2 Hz, 1H), 4.06 (s, 3 H), 400 (s, 3 H), 3.83 (s, 3 H), 2.60 (m, 1 H), 2.52 (s, 3 H), 2.38-2.27 (m, 2 H), 1.94–1.87 (m, 1 H), $^{13}$C NMR ($CDCl_3$, 75.5 MHz): δ168.0, 152.1, 148.3, 147.5, 140.9, 140.3, 133.9, 131.9, 120, 118.0, 117.6, 116.9, 102.2, 100.7, 81.7, 62.1, 60.7, 59.3, 56.7, 49.9, 46.2, 27.9.

EXAMPLE 2

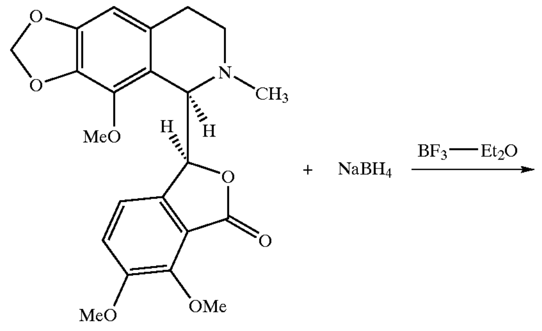

1

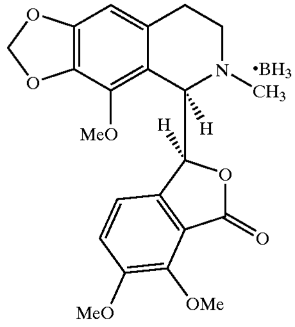

2

The synthesis of borane-(S, R)-noscapine complex (2)

(S, R)-Noscapine 1 (830 mg, 2.0 mmol, 1.0 equiv.) was dissolved in 10 mL of $BF_3$-$Et_2$ O. This solution was dropped slowly at 0° to a solution of $NaBH_4$ (150 mg, 4.0 mmol, 2.0 equiv.) in 14 mL dry THF and stirred at 0° for 1 h under $N_2$. Then it was refluxed for 2 h. After cooling to room temp, the solution was poured into ice water and extracted with $CHCl_3$ (70 mLx2). The organic phase was washed with brine, dried with MgSO4 and concentrated. The resulting oil was purified by flash chromatography ($SiO_2$, 3x15 cm, 50% EtOAc in hexane) to give 2 as a white solid (444 mg, 52%), TLC (silica gel, 65% EtOAc in hexane, Rf=0.75); $^1$H NMR ($CDCl_3$, 300 MHz): δ7.41 (d, J=8.1 Hz, 1 H), 7.31 (d, J=8.1 Hz, 1 H), 6.83 (s, 1 H), 6.33 (s, 1 H), 5.81 (dd,J=12.9 Hz, 0.9 Hz, 2 H), 4.54 (s, 1 H), 3.99 (s, 3 H), 3.92 (s, 3 H), 3.73 (m, 1 H), 3.20 (s, 3 H), 3.15 (m, 2 H), 2.93 (m, 1 H), 2.61 (s, 3H).

EXAMPLE 3

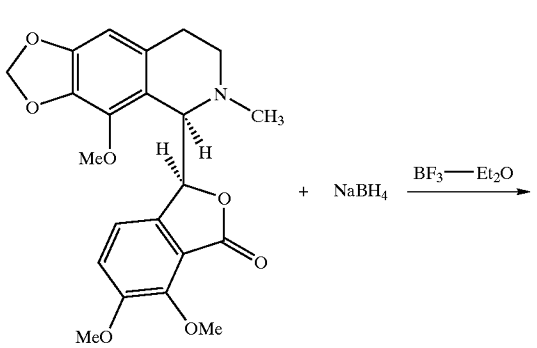

1

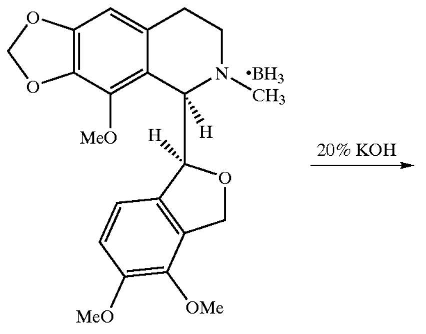

2

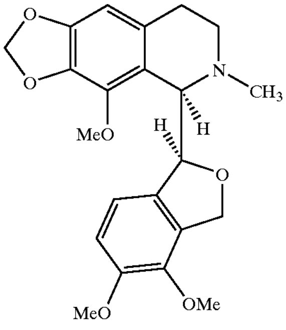

3

Compound 3 and 4 Were Prepared by Literature Method Prior, S.; Wiegrebe, W. *Arch. Pharm.* 1983, 316, 737.

The synthesis of 1,3-dihydro-4,5-dimethoxy-1-[1-(8-methoxy-2-methyl-6,7-methylenedioxy-1,2,3,4-tetrahydroisoquinolinyl)] isobenzofuran-$BH_3$ (3)

(S,R)-Noscapine (830 mg, 2.0 mmol, 1.0 equiv.) was dissolved in 10 mL of $BF_3$-$Et_2O$. This solution was dropped slowly at 0° C. to a solution of $NaBH_4$ (150 mg, 4.0 mmol, 2.0 equiv.) in 18 mL dry THF and stirred at 0° C. for 1 h under $N_2$. Then it was refluxed for 4 h. After cooling to room temp, the solution was poured into ice water and extracted with $CHCl_3$ (70 mLx2). The organic phase was washed with brine, dried with $MgSO_4$ and concentrated. The resulting oil was purified by flash chromatography ($SiO_2$, 3x15 cm, 50% EtOAc in hexane) to give 3 as a white solid (686 mg, 83%). TLC (silica gel, 50% EtOAc in hexane, R*f*=80); IR ($CH_2Cl_2$, NaCl, $cm^{-1}$) 2371 (s), 1616 (w). $^1H$ NMR ($CDCl_3$, 300 MHz): δ7.15 (d, J=8.4 Hz, 1 H), 6.93 (d, J=8.1 Hz, 1 H), 6.57 (br s, 1 H), 6.33 (s, 1 H), 5.79 (AB, J=1.5 Hz, 1 H), 5.74 (AB, J=1.5 Hz, 1 H), 4.81 (d, J=1.20 Hz, 1 H), 4.34 (s, 1 H), 4.07 (dd, J=12.3 Hz, 2.7 Hz, 1 H), 3.85 (s, 3 H), 3.71 (s, 3 H), 3.16 (s, 3 H), 3.05-2.81 (m, 4 H), 2.53 (s, 3 H). HRMS (FAB) Calcd for $C_{22}H_{28}BLiN0_6$ $(M+Li)^+$: 420.2170, Found 420.2173.

The synthesis of 1,3-diliydro-4,5-dimethoxy-1-[1-(8-methoxy-2-methyl-6,7-methylenedioxy 1,2,3,4-tetrahydroixoquinolinyl)]isobenzofuran (4)

Compound 3 (450 g, 1.10 mmol) was refluxed in 15 mL of 20% aqueous KOH solution for 2 h. The reaction mixture was cooled to room temp, neutralized with 2 N HCl to PH=7 and extracted with $CHCl_3$. The organic phase was washed with brine, dried with MgSO4 and concentrated. Compound 4 was crystallized from $Et_2O$ (220 mg, 50%). $^1H$ NMR ($CDCl_3$, 300 MHz): delta 6.72 (d, J=8.4 Hz, 1 H), 6.32 (s, 2 H), 5.88 (m, 2 H), 5.63 (br s, 1 H), 5.0 (br s, 2 H), 4.40 (br s, 1H), 3.82 (s, 3 H), 3.81 (s, 3 H), 3.14 (br s, 1 H), 2.64 (br s. 3 H), 2.60–2.43 (m, 3H).

EXAMPLE 4

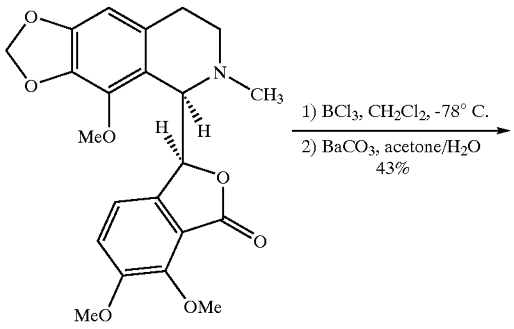

1

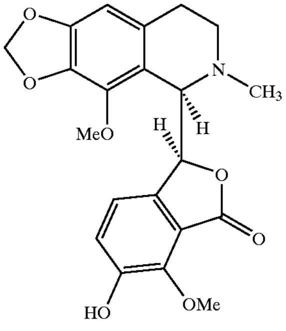

5

The synthesis of compound 5

(S;R)-Noscapine (826 mg, 2.0 mmol, 1.0 equiv.) was dissolved in 25 mL of $CH_2Cl_2$. This solution was added dropwise to a 1.0 M solution of borane trichloride in $CH_2Cl_2$ (8.0 mL, 8.0 mmol, 4.0 equiv.) at −78° C. After 5 h, the reaction was quenced with saturated aqueous NaHCO3 (10 mL) and warmed to room temp. The reaction mixture was extracted with EtOAc (50 mLx3), the combined organic phases were washed with brine (40 mL ), dried with $MgSO_4$ and concentrated.

The obtained white solid was dissolved in acetone (50 mL) and $H_20$ (25 mL). This solution was treated with barium carbonate (1.55 g. 7.84 mmol) and refluxed for 3 h. After cooling to room temp, the reaction mixture was filtered. The filtrate was treated with 1 N HCl until PH=2, then extracted with EtOAc (50 mLx3). The combined extracts were washed with brine, dried over $MgSO_4$ and concentrated. Crystallization ($CH_2Cl_2$-$Et_20$) was performed for the resulting off-white solid to give 5 as a silver gray solid (340 mg, 43%). IR ($CH_2Cl_2$, NaCl, $cm^{-1}$) 3431 (s), 1767 (s). $^1H$ NMR ($CDCl_3$, 300 MHz): δ7.57 (br s, 1 H), 7.27 (br s, 1H), 6.57 (br s, 1 H), 6.33 (s, 1 H), 5.82 (s, 1 H), 5.78 (s, 1H), 5.11 br, 1 H), 4.08 (br s, 1 H), 3.94 (s, 3 H), 3.87

(s, 3 H), 3.33 (m, 1 H), 3.20 (s, 3H), 3.00 (m, 1 H), 2.82 (m, 2 H). $^{13}C$ NMR ($CDCl_3$, 75.5 MHz): δ166.3, 152.4, 150.1, 147.3, 139.8, 138.9, 133.4, 126.2, 119.3, 118.8, 116.9, 106.7, 102.3, 100.9, 78.5, 61.9, 58.2, 56.8, 45.2, 39.9, 21.4.

EXAMPLE 5

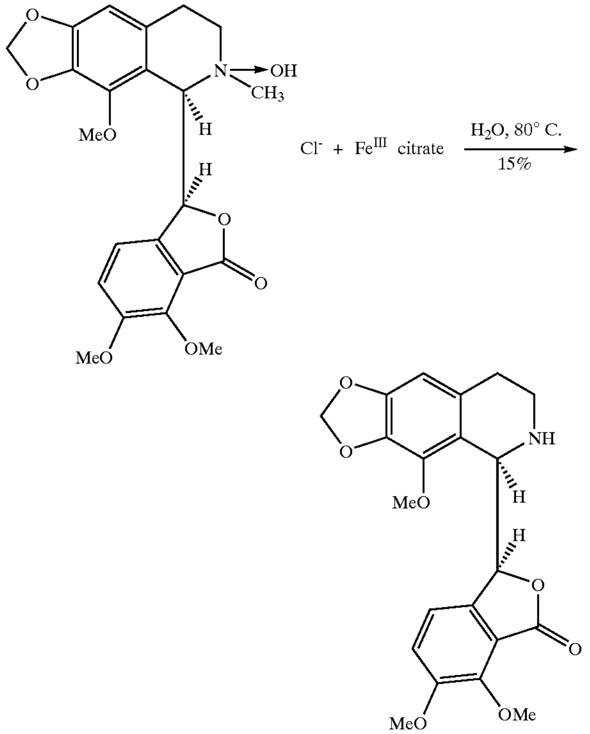

6

Ferric citrate (10.5 g) was dissolved in 200 mL of $H_20$. Citric acid was added to make pH=2. This solution added to noscapine N-oxide HCl salt (6.0 g)[Uhrin, D. et al., Collect. Czech.Chem. Commun. 54:498(1989)] and the mixture was heated to 85° C. for 3 h. After cooling to room temp, the solution was treated with saturated $Na_2CO_3$ solution until pH=9 and extracted with $CHCl_3$ (200 mL×4). The combined organic phases were washed with brine, dried with anhydrous $MgSO_4$ and concentrated. The resulting oil was purified by flash chromatography ($SiO_2$, 3×25 cm, 75% EtOAc in hexane) to give 6 as a yellow oil (793 mg, 15%). TLC (silica gel, 75% EtOAc in hexane, $R_{£}$,=0.25); IR ($CH_2Cl_2$, NaCl, $cm^{-1}$) 3370 (w), 1758 (s); $^1H$ NMR ($CDCl_3$, 300 MHz):): δ6.92 (d, J=8.1 Hz, 1 H), 6.29 (s, 1 H), 5.93–5.91 (m, 3 H), 5.87 (d, J=3.9 Hz, 1 H), 4.80 (d, J=3.9 Hz, I H), 4.04 (s,3 H), 4.02 (s, 3 H), 3.80 (s, 3 H), 2.59–2.55 (m, 1 H), 2.50–2.38 (m, 1 H), 2.30–2.22 (m, 1 H), 2.15–2.07 (m, 1 H), 1.96 (br s, 1 H). $^{13}C$ NMR ($CDCl_3$, 75.5MHz):): δ168.4, 152.1, 148.3, 147.8, 141.0, 140.3, 134.1, 131.9, 119.5, 118.4, 117.5, 116.9, 103.1, 100.7, 80.6, 62.2, 59.4, 56.6, 52.7, 39.5, 29.6. HRMS (FAB) Calcd for $C_{21}H_{21}$ $LiNO_7$ $(M+Li)^+$: 406.1478, Found 406.1477. Anal. Calcd. for $C_{21}$ $H_{21}$ $N0_7$: C, 63.15; H, 5.30; N, 3.51. Found: C, 63.35; H, 5.45; N, 3.42.

EXAMPLE 6

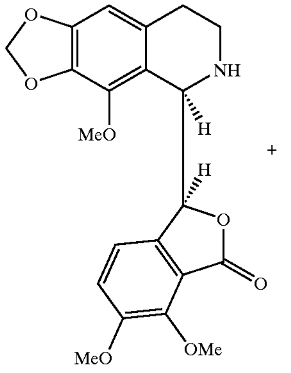

6

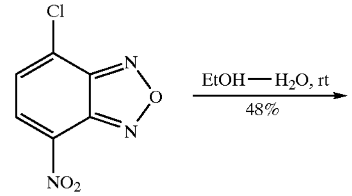

(NBD-Cl)

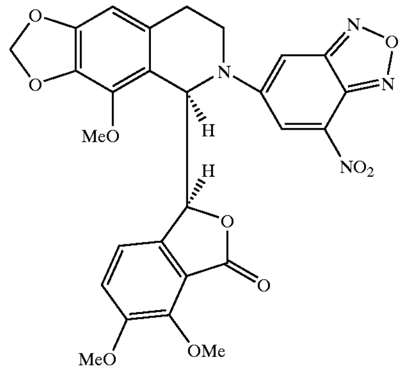

7

To an ETOH (15 mL) solution of amine 6 (160 mg, 0.40 mmol, 1.0 equiv.) was added 30 mL of $Na_2B_4O_7$ (1.14 g) buffer and NBD-CL (80 mg, 0.4 mmol, 1.0 equiv.). The reaction mixture was stirred at room temp for 15 h. Evaporation of ETOH left a dark orange slurry which was extracted with $CHCl_3$ (70 mL×2). The combined organic phases were washed with brine, dried with $MgSO_4$ and concentrated. The resulting green oil was purified by flash chromatography ($SiO_2$, 3×15 cm, 65% EtOAc in hexane) to give an orange solid which was recrystallized from $CH_2Cl_2$ and hexane to give 7 as an orange crystal (108 mg, 48%). TLC (silica gel, 65% EtOAc in hexane, $R_{535}$ =0.65); mp=194–195° C. ($CH_2Cl_2$/hexane); IR ($CH_2Cl_2$, NaCl, $cm^{-1}$) 1765 (s) 1616 (m), 1540 (s), 1500 (s), 1287 (s), 1261 (m). $^1H$ NMR ($CDCl_3$, 300 MHz):): δ8.53 (d, J=9.0 Hz, 1 H), 7.41 (br d, J=7.8 Hz, 1 H), 7.29 (d, J=8.4 Hz, 1 H), 7.00 (br s, 1 H), 6.48 (d, J=2.7 Hz, 1 H), 6.44 (s, 1 H), 6.04 (d, J=2.7 Hz, 1 H), 5.90 (d, J=7–5 Hz, 2 H), 4.02 (s, 3 H), 3.95 (s, 3 H), 3.81 (m, 1 H), 3.76 (s, 3 H), 3.70–3.50 (m, 2 H), 3.02–2.93 (m, 1 H). $^{13}C$ NMR($CDCl_3$, 75.5 MHz): ): δ166.7, 152.8, 149.6, 147.9, 145.1, 145.0, 144.7, 139.5, 138.7, 135.3, 133.7, 130.4, 123.7, 119.0, 118.7, 118.1, 113.4, 102.9, 102.4, 100.9, 81.9, 62.2, 59.1, 58.1, 56.8, 46.5, 27.8, HRMS (FAB) Calcd for $C_{27}H_{22}LiN_4O_{10}$ (M+Li)+: 569.1496, Found 569.1472. Anal. Calcd. for $C_{27}H_{22}N_4O_{10}$: C, 57.65; H, 3.91; N, 9.96. Found: C, 57.85; H, 4.04; N, 9.81.

EXAMPLE 7

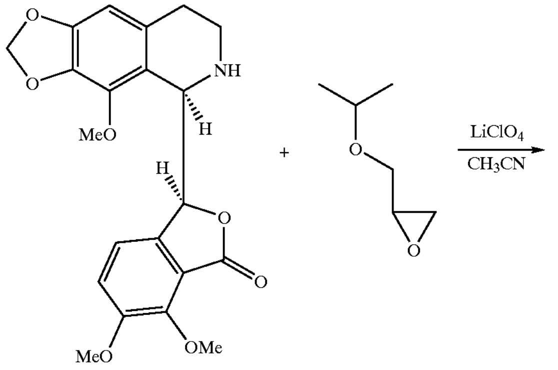

6

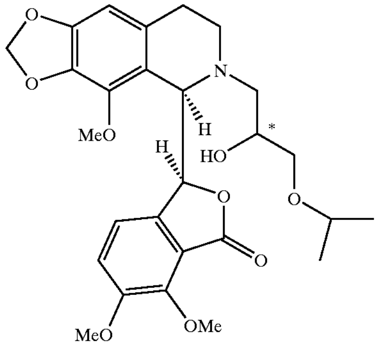

8

A $CH_3CN$ (2 mL) solution of glycidyl isopropyl ether (50 μL, 0–40 mmol, 1.0 equiv.) was treated with anhydrous $LiCl_4$ salt (43 mg, 0.40 mmol, 1.0 equiv.) and stirred for about 10 min. until a clear solution was observed. This solution was treated with an $CH_3CN$ (3 mL) solution of compound 6 (160 mg, 0.40 mmol, 1.0 equiv.) at room temp. The mixture was refluxed for 24 h, cooled to room temp., washed with $H_20$ and extracted with $Et_2O$ (40 mL×3). The combined organic phases were washed with brine, dried with $MgSO_4$ and concentrated. The resulting orange oil was purified by flash chromatography ($SiO_2$, 2×15 cm, 50% EtOAc in hexane) to give 8 as a yellow oil which is a mixture of the two diasteoromers (1:1 ratio, 172 mg, 83%). TLC (silica gel, 50% EtOAc in hexane, $R_{535}$ =O0.50); IR ($CH_2Cl_2$, NaCl, $cm^{-1}$) 3450 (m), 1761 (s), 1498 (m), 1478 (m), $^1H$ NMR ($CDCl_3$, 300 MHz): ): δ6.96 (d, J=8.4 Hz, 2 H), 6.30 (s, 2 H), 6.24 (t, J=8.4 Hz, 2 H), 5.90 (s, 4 H), 5.73 (d, J=4.5 Hz, 1 H), 5.67 (d, J=4.2 Hz, 1 H), 4.47 (d, J=4.2 Hz, 1 H), 4.42 (d, J=4.5 Hz, 1 H), 4.06 (s, 3 H), 4.05 (S. 3 H), 3.97 (s, 3 H), 3.96 (s, 3H), 3.82 (s, 6 H), 3.56 (d of sept, J=6.0 Hz, 2 H), 3.41 (m, 4 H), 3.0 (br s, 2 H), 2.74–2.00 (m, 14 H), 1.12 (t, J=5.7 Hz, 12 H). $^{13}C$ NMR ($CDCl_3$, 75.5 MHz): ): δ167.9, 1167.8, 152.2 (2 C), 148.5 (2 C), 148.1 (2 C), 141.2, 141.0, 140.5, 140.4, 133.8, 133.7, 130.9, 130.5, 119.3, 119.0, 118.4(2 C), 117.5 (2C), 116.3, 115.8, 102.7, 102–6, 100.7, 100.6, 80.8, 80.1, 71.9, 71.8, 70.4, 70.1, 68.0, 67.8, 62.3, 62.2, 60.5 (2 C), 59.4, 59.2, 58.6, 58.5, 56.7 (2 C), 46.2, 44.7, 24.8, 24.3, 22.0 (2 C), 21.9 (2 C). Anal. Calcd. for $C_{27}H_{33}NO_9$: C, 62.90; H, 6.45; N,2.72; Found: C, 62.97; H, 6.45; N, 2.64.

EXAMPLE 8

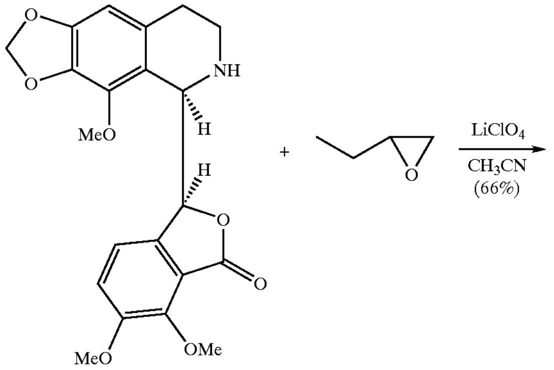

6

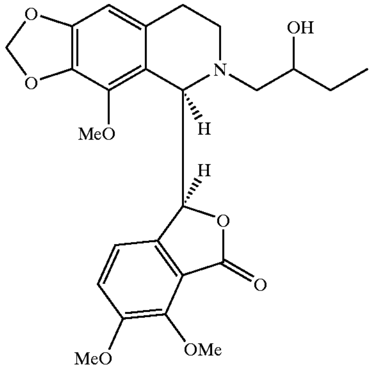

9

An $CH_3CN$ (2 mL) solution of 1,2-epoxybutane (114 μL, 1.32 mmol, 3.3 equiv) in a sealed tube was treated with anhydrous $LiClO_4$ salt (43 mg, 0.40 mmol, 1.0 equiv) and stirred for 10 min until a clear solution was observed. This solution was treated with an $CH_3CN$ (3 mL) solution of compound 6 (160 mg, 0.40 mmol, 1.0 equiv) at room temp. The mixture was heated at 115° C. for 10 h, cooled to room temp, washed with $H_20$ and extracted with $Et_2O$ (50 mL×3). The combined organic phases were washed with brine, dried with $MgSO_4$ and concentrated. The resulting yellow oil was purified by flash chromatography ($SiO_2$, 2×15 cm, 65% EtOAc in hexane) to give 9 as a light yellow oil which is a mixture of the two diasteoromers (1:1 ratio, 125 mg, 66%). TLC (silica gel, 65% EtOAc in hexane, $R_£$=0.60); IR ($CH_2Cl_2$, NACl, $cm^{-1}$) 3523 (s), 1758(s), 1622 (m), $^1H$ NMR ($CDCl_3$, 300 MHz): ): δ6.99 (d, J=8.1 Hz, 2 H), 6.31 (s, 1 H), 6.30 (s, 1 H), 6.26 (d, J=8.4 Hz, 1 H), 6.25 (d, J=8.4 Hz, 1 H), 5.90 (s, 4 H), 5.79 (d, J=4.5 Hz, 1 H), 5.68 (d, J=3.9 Hz, I 1H), 4.48 (d, J=3.9 Hz, 1 H), 4.40 (d, J=4.5 Hz, 1 H), 4.07 (s, 3 H), 4.06 (s, 3 H), 3.98 (s, 6 H), 3.83 (s, 6 H), 3.66–3.53 (m, 2 H), 3.20 (br s, 2 H), 2.68–2.38 (m, 8 H), 2.23–2.10 (m, 4 H), 1.42 (m, 4 H), 0.95 (t, J=6.9 Hz, 3 H), 0.93 (t, J=7.2 Hz, 3 H). $^{13}C$ NMR ($CDCl_3$, 75.5 MHz):): δ168.0, 167.7, 152.3, 152.2, 148–6 (2 C), 148.2, 148.1, 141.2, 140.9, 140.6, 140.3, 133.9, 133.7, 130.9, 130.1, 119.3, 118.8, 118.5 (2 C), 117.4 (2 C), 116.4, 115.4, 102.8, 102.5, 100.7, 100.6, 81.1, 79.6, 68.9, 68.7, 62.5, 62.3, 62.2, 61.3, 61.2, 59.3, 59.2, 57.5, 56.7 (2 C), 46.4, 44.0, 27.5, 27.1, 25.1, 23.7, 10.0, 9.8. Anal. Calcd. for $C_{25}H_{29}NO_8$: C, 63.68; H, 6.20; N, 2.97. Found: C, 63.68; H, 6.1 8; N, 2.90.

EXAMPLE 9

Noscapine Arrests Hela and Thymocyte Cells at M Phase

Hela cells were grown in DMEM supplemented with 10% fetal calf serum, 1 mM L-glutamine and 1% penicillin/ streptomycin. The tumor cell line E-G7-OV A (H-$2^h$) [Moore, M. W., et al., *Cell.* 54, 777 (1988)] was grown in RPM1 1640 with 10% fetal calf serum, 1% sodium pyruvate, 1 mM L-glutamine, 0.1% gentamycin, 50 $\mu$tM β-mercaptoethanol. Cells were grown at 37° C. in a 5% $CO_2$ atmosphere. Cell viability was assessed by trypan blue exclusion analysis. Cell numbers were determined using a hemacytometer, C57BL/6 (H-$2^h$) mice, 8 to 12 weeks of age, were obtained from Harian Sprague Dawley, Inc. (Indiananapolis, Ind.). Mice were maintained on standard laboratory chow and water ad libitum, in a temperature and light controlled environment. For immunofluorescence, both Hela and thymocyte cells were treated identically except the Hela cells were grown onto glass coverslips while EL4 thymocytes were put on glass coverslips after fixation.

Cells in 10 ml medium were incubated with 2 $\mu$l DMSO or 20 $\mu$M Noscapine (2 $\mu$l 0.1 M DMSO solution) respectively. After 24 hr, cells were fixed with cold (−20° C.) methanol for 5 min., then rehydrated by PBS for 1 min. Nonspecific sites were blocked by incubating with 200 $\mu$l of 1% bovine serum albumin (BSA) in phosphate buffered saline (PBS) at 37° C. for 15 minutes. A mouse monoclonal antibody against α-tubulin was diluted 1:200 in PBS containing 1% BSA and incubated (200 $\mu$l) with the coverslips at 37° for 1 hr.

Then cells were washed with 1% BSA-PBS solution for 10 min. at room temperature before incubating with a 1:200 dilution of a rhodamine labeled goat anti-mouse IgG antibody at room temperature for 45 min., then the coverslips were rinsed by 1% BSA/PBS solution for 10 min. and labeled by DAPI (4', 6-diamino-2-phenyliudole) for another 10 min. at room temperature. The coverslips containing the cells were then mounted with a solution containing 0.01% 1,4-diazobicyclo (2,2,2) octane. Cells were examined with a fluorescence microscope. The flow cytometric evaluation of the cell cycle status was performed according to a modification of as described in Empey, D. W., et al., Eur. J. Clin. Pharmacol. 16, 393 (1979). Briefly, untreated or noscapine-treated cells were centrifuged, washed twice with ice-cold PBS, and fixed in 70% ethanol. Tubes containing the cell pellets were stored at −20° C. for at least 24 hr. Following this, the cells were centrifuged at 1000×g for 10 min. and supernatant was discarded. The pellets were resuspended in 30 $\mu$l phosphate-citrate buffer at room temperature for 30 min. Cells were then washed with 5 ml PBS and incubated with propidiun iodide and RNase (20 mg/ml PI and 20 mg/ml RNase A in PBS) for 30 min. The samples were read on a cytometer.

Results show that by immunofluorescence, with an antibody specific for alpha-tubulin, that after treatment with noscapine, microtubule arrays are arrested in M phase in Hela and thermocyte cells. Flow cytometric analysis of DNA content showed consistent results.

EXAMPLE 10

Noscapine Initiates Apoptosis

Oligonucleosomal fragmentation of genomic DNA was determined according to Walton, M. I. et. al., Cancer. Res. 53, 1853 (1993). An aliquot of 3.3×$10^6$ cells in 10 ml medium was incubated with 20 $\mu$1 M Noscapine (2 $\mu$0.1 M DMSO solution) for different time periods ranging from 0 to 24 hr. At the end of incubation, cells were pelleted and washed twice with ice-cold PBS, and lysed in 250 $\mu$l 1% (v/v) NP-40 detergent containing 0.5 mg/ml proteinase K in PBS solution on ice for 60 min. Samples were centrifuged, and the supernatants were removed and incubated with 5 $\mu$l 10 mg/ml Rnase A at 37° C. for 40 min. An aliquot of 1 ml anhydrous ethanol was added, tubes were placed at −20° C. for 20 min., then centrifuged to pellet DNA. After the samples were dry, the same amount of DNA (10 $\mu$g) was electrophoresed at 80V for 3 hr. through a 2% agarose gel containing ethidium bromide in TAE buffer. DNA bands were visualized under HV light. A 123 bp DNA ladder was used as molecular size marker.

Morphological changes in the nuclear chromatin of cells undergoing apoptosis were detected by staining with 4', 6-diamidino-2-phenylindole (DAPI). In brief, 0.5×$10^6$ to 3×$10^6$ cells were fixed with 4% glutaraledehyde, 0.2% Triton x-100, in PBS and incubated at room temperature for 10 min., then centrifuged at 1000×g for 10 min., resuspended in 20 $\mu$l 0.1% DAPI ethanol. Following 15 min. incubation at room temperature, a 10 $\mu$l aliquot was placed on a glass slide, and 400 cells per slide were scored for the incidence of apoptotic chromatin changes with a fluorescence microscope. A TdT-Mediated dUTP nick end labeling assay is used according to Gorczyca, W. et al., Cancer Res. 53, 1945 (1993) and Gavrieli, Y. et al., J. Cell Bio. 119, 493 (1992). An aliquot of 2×$10^6$ cells in 10 ml medium were respectively incubated with 2 $\mu$l DMSO and 20 $\mu$M noscapine (2 $\mu$l 0.1 M DMSO solution) for 24 hr.

Cells were pelleted and washed with ice-cold PBS twice, lymphocyte cells were fixed in 4% paraformaldehyde in PBS and air dried. The slides were rinsed with PBS and incubated with blocking solution (0.3% $H_2O_2$ in methanol) for 30 min. at room temperature. The slides were rinsed with PBS again and incubated in permeability solution (0.1% Triton x-100 in 0.1% sodium citrate) on ice for 2 min. Then the slides were washed twice with PBS, then 50 $\mu$l nick end labeling assay reaction mixture was added on samples and the slides were incubated in a humidified chamber for 60 min. at 37° C.

After the slides were rinsed with PBS, 50 $\mu$l converter-POD solution was added on samples and incubated for 30 min. at 37° C. The slides were rinsed with PBS for 3 times, then 60 $\mu$l DAB substrate solution was added on the samples, and the slides were incubated at room temperature for 10 min. After the slides were rinsed with PBS for another 3 times, coverslips were mounted and analyzed with a light microscope.

Results show progressive DNA degradation with increasing time of noscapine treatment, as measured by gel electrophoresis of fragmented genomic DNA, or by staining of treated cells.

EXAMPLE 11

Inhibition of Tumor Growth by Noscapine

C57BL/6 mice were injected subcutaneously in the right flank with 2×$10^6$ E.G7-OVA cells. Three days later, mice were injected intraperitoneally, every day for three weeks, either with 200 $\mu$l saline (n=10), or with 3 mg noscapine dissolved in 200 $\mu$l saline (n=10),. Third group of mice (n=10) was fed 3 mg noscapine via intragastric (i.g.) intubation using a 1 ml syringe fitted with a 20 gauge stainless steel ball point needle. After three weeks, all mice were sacrificed by cervical dislocation. Tumors were removed and weighted. Tumor weights were individually plotted and comparisons between control and treatment groups were analyzed by the Student's test. Statistical differences were considered significant if p values were less than 0.01. Results showed that mice treated with noscapine had significantly reduced tumor weight.

EXAMPLE 12

Noscapine Causes Apoptosis in Solid Lymphoid Tumors Induced in Mice

Microscopic examination of Haemotoxline and Eosine stained cells showed many cells in noscapine treated mice with apoptotic morphologies.

EXAMPLE 13

Noscapine Induces Conformational Change Upon Binding Tubulin and Promotes Microtube Assembly Phosphocellulose purified bovine brain tubulin was employed throughout these biophysical experiments. Fluorescence titration for determining binding constants was performed according to Peyrot, V. et al., Biochemistry 31, 11125 (1992). In brief; at room temperature, 2 μM tubulin in 100 mM PIPES, 2 mM EGTA, 1 mM $MgCl_2$ was excited at 278 nm, and the fluorescence emission spectra were recorded with bandwidths 2 nm. The fluorescence emission intensity of noscapine at this excitation wavelength was negligible and at the concentration of noscapine used it gave no appreciable inner filter effect. The concentration of noscapine was raised in increments of 0.5 μM, until the decrease in the fluorescence intensity was saturated. The value of the dissociation constant and the number of sites were obtained from Scatchard plots using the equation, $r/[L]_{free}=n/K^{d}-/K_{d}$, where r is the ratio of the concentration of bound ligand to the total protein concentration and n is the number of binding sites. Circular dichroism (CD) spectra measurements were performed in a spectroscometer, in cells (0.1 cm path) at 25° C. Microtubule assembly was recorded on a spectrophotometer with thermocontroler. The cuvettes (0.4 cm path) containing 100 mM PIPES, 2 mM EGTA, 1 mM $MgCl_2$ and 1 mM GTP (G-PEM buffer), and 20 μM noscapine/DMSO were kept at room temperature before addition of tubulin and shifting to 37° C. Tubulin and noscapine in G-PEM buffer did not show any detectable absorption at 350 nm. The assembly was monitored by measuring the changes in turbidity at 0.5 min. intervals. Noscapine was dissolved in DMSO at 0.8 mM and stocked at 4° C. The final concentration of DMSO was 2.5%.

Results show that noscapine affords fluorescence quenching of tubulin. Scatchard plot analysis showed an apparent dissociation constant ($K_d$) of ' $1.86\pm0.34\times10^{-6}$ M and a stoichiometry of 0.95±0.02 noscapine molecule per complex of tubulin subunit. There is also saturation of the noscapine induced quenching in tubulin fluorescence intensity. Noscapine promotes tubulin assembly, as measured by increased absorbance at 350 nm of tubulin when treated with noscapine.

EXAMPLE 14

Initiation of Apoptosis by Noscapine and Derivatives

Morphological changes in the nuclear chromatin of HL-60 cells undergoing apoptosis were detected by staining with 4', 6-diamidino-2-phenylindole (DAPI). In brief, $0.5\times10^{6}$ to $3\times10^{6}$ cells were fixed with 4% glutaraledehyde, 0.2% Triton x-100, in PBS and incubated at room temperature for 10 min., then centrifuged at 1000x9 for 10 min., resuspended in 20 μl 0.1% DAPI ethanol. Following 15 min. incubation at room temperature, at 10 μl aliquot was placed on a glass slide, and 400 cells per slide were scored for the incidence of apoptotic chromatin changes with a fluorescence microscope.

Results show that noscapine, compound 3 and compound 4 initiate apoptosis.

| Compound* | Apoptic Cell Percentage |
|---|---|
| Noscapine, 20 μM in DMSO | 30, 17† |
| 3, 20 μm in DMSO | 37, 28 |
| 4, 20 μ in DMSO | 48, 32 |
| Noscapine, 50 μM in DMSO | 27 |
| 3, 50 μM in DMSO | 39 |
| 4, 50 μM in DMSO | 52 |

*All compounds were incubated with HL-60 cells at the indicated final concentrations for 24 hours.
†Two trials were conducted at 20 M, the result for each trial is shown.

While the foregoing specification teaches the principles of the present invention, with examples provided for the purpose of illustration, it will be understood that the practice of the invention encompasses all of the usual variations, adaptations, modifications or deletions as come within the scope of the following claims and its equivalents.

What is claimed is:

1. A delivery system for the treatment of neoplastic diseases, comprising a composition comprising a compound of the formula

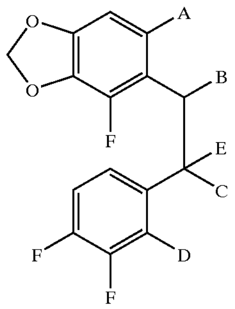

wherein

A is

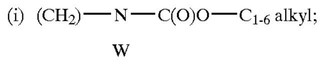

and W is $C_{1-6}$ alkyl; or

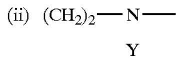

and forms a six membered ring with B, said ring containing one nitrogen;

Y is (a) $C_{1-6}$ alkyl, or H;

(b) C(O)—$C_{1-6}$ alkyl;

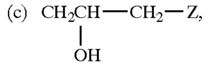

wherein Z is $C_{1-6}$ alkyl or O—$C_{1-6}$ alkyl;

(d) aryl; or (e) heterocycle;

B is a single bond, OH or halo;

C is —OH, —$CH_2$—, —O—, or forms a 5-membered lactone or lactam ring with D; and D is:

(i) —OH, —$CH_2$-halo, —CH(O), —COOH, —C(O)—O—$C_{1-6}$ alkyl, —$(CH_2)_n$—, —CHOH—, wherein n is an integer and is 1, 2, or 3; or (ii) forms a 5-membered lactone or lactam ring with C;

E is —H or —$CH_3$; and

F is —OH or —$OCH_3$, or pharmaceutically acceptable salts thereof, and a controlled-release mechanism for providing prolonged delivery of the composition, whereby the delivery system enhances the delivery of the composition to a patient in need thereof.

2. The delivery system of claim 1, wherein the controlled-release mechanism is selected from the group consisting of implantable devices, delivery pumps, wafers, biodegradable polymers, and combinations thereof.

3. The delivery system of claim 1, wherein the controlled-release mechanism is a topical formulation.

4. The delivery system of claim 3, where in the topical formulation is selected from the group consisting of gels, lotions, patches, iontophoresis solutions, and combinations thereof.

5. The delivery system claim 1, wherein the controlled-release mechanism comprises a modified form of the compound.

6. The delivery system of claim 1, wherein the controlled-release mechanism comprises a modification that enhances the permeability of the composition through a patient's blood-brain barrier.

7. The delivery system of claim 6, wherein the controlled-release mechanism comprises the delivery of a substance that at least temporarily shrinks the cells of the blood-brain barrier to allow increased passage of the composition.

8. The delivery system of claim 1, wherein the compound is modified by the addition of a peptide drug transporter.

9. The delivery system of claim 1, wherein the controlled-release mechanism comprises a modification to the compound to enhance its tumor targeting ability.

10. The delivery system of claim 9, wherein the compound is modified by packaging the compound into an agent capable of binding to tumor cell receptors such that the compound is adapted to selectively enter tumor cells.

11. The delivery system of claim 9, wherein the compound is modified by liposomal encapsulation.

12. The delivery system of claim 11, wherein the compound is complexed with cyclodextrins and encapsulated by liposomes.

13. The delivery system of claim 9, wherein the compound is modified with tumor specific antibodies or ligands for tumor specific proteins.

14. The delivery system of claim 9, wherein the compound comprises an adduct for the compound or its derivatives for tumor targeting purposes.

15. The delivery system of claim 1, wherein the composition is delivered via oral delivery, rectal delivery, nasal delivery, parenteral delivery, direct tissue injection, topical delivery, intracranial delivery, or combinations thereof.

16. The delivery system of claim 15, wherein the parenteral delivery comprises subcutaneous delivery, intravenous delivery, intramuscular delivery, intraperitoneal delivery, infrasternal injection, or infusion.

17. The delivery system of claim 1, wherein the neoplastic disease is selected from the group consisting of cancer of the colon, non-small cell lung cancer, cancer of the brain, ovarian cancer, cancer of the kidney, cancer of the prostate, leukemia, breast cancer, skin cancer, melanoma, and cancer of the bladder.

18. The method of claim 1, wherein the compound is noscapine.

19. A method for the treatment of neoplastic diseases, comprising:

(a) administering to a mammal in need of such treatment an effective amount of a composition comprising a compound of the formula

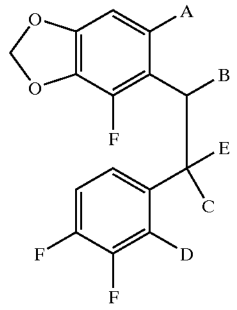

wherein:

A is (i) 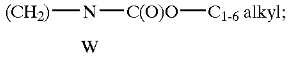

and W is $C_{1-6}$ alkyl; or (ii) 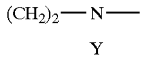

and forms a six membered ring with B, said ring containing one nitrogen;

Y is (a) $C_{1-6}$ alkyl, or H;

(b) C(O)—$C_{1-6}$ alkyl;

(c) 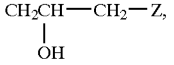

wherein Z is $C_{1-6}$ alkyl or O—$C_{1-6}$ alkyl;

(d) aryl; or (e) heterocycle;

B is a single bond, OH or halo;

C is —OH, —$CH_2$—, —O—, or forms a 5-membered lactone or lactam ring with D; and D is:

(i) —OH, —$CH_2$-halo, —CH(O), —COOH, —C(O)—O—$C_{1-6}$ alkyl, —$(CH_2)_n$—, —CHOH—, wherein n is an integer and is 1, 2, or 3; or (ii) forms a 5-membered lactone or lactam ring with C;

E is —H or —$CH_3$; and

F is —OH or —$OCH_3$, or pharmaceutically acceptable salts thereof, in combination with one or more of radiation therapy, phototherapy, surgical resection, immunotherapy, vaccination, interferon treatment, or stereotactic surgery for the treatment or prevention of tumors.

20. The method of claim 19, wherein the composition is used as a preventive measure after surgical excision.

21. The method of claim 19, wherein the compound is noscapine.

* * * * *